United States Patent
Johnson et al.

(10) Patent No.: US 11,554,122 B2
(45) Date of Patent: Jan. 17, 2023

(54) FUSED PENTACYCLIC IMIDAZOLE DERIVATIVES AS MODULATORS OF TNF ACTIVITY

(71) Applicants: UCB Biopharma SRL, Brussels (BE); SANOFI, Paris (FR)

(72) Inventors: James Andrew Johnson, Slough (GB); Ellen Olivia Gallimore, Slough (GB); Mengyang Xuan, Slough (GB)

(73) Assignees: UCB BIOPHARMA SRL, Paris (FR); SANOFI, Paris (FR)

( * ) Notice: Subject to any disclaimer, the term of this patent is extended or adjusted under 35 U.S.C. 154(b) by 0 days.

(21) Appl. No.: 17/284,950

(22) PCT Filed: Oct. 23, 2019

(86) PCT No.: PCT/EP2019/078922
§ 371 (c)(1),
(2) Date: Apr. 13, 2021

(87) PCT Pub. No.: WO2020/084008
PCT Pub. Date: Apr. 30, 2020

(65) Prior Publication Data
US 2021/0361668 A1   Nov. 25, 2021

(30) Foreign Application Priority Data
Oct. 24, 2018   (EP) .................................... 18275165

(51) Int. Cl.
*A61K 31/55* (2006.01)
*C07D 471/18* (2006.01)
*C07D 487/18* (2006.01)

(52) U.S. Cl.
CPC ............ *A61K 31/55* (2013.01); *C07D 471/18* (2013.01); *C07D 487/18* (2013.01)

(58) Field of Classification Search
CPC .............................. A61K 31/55; C07D 487/18
USPC ...................................... 514/211.04; 540/520
See application file for complete search history.

(56) References Cited

FOREIGN PATENT DOCUMENTS

| WO | WO 2013/186229 | 12/2013 | | |
|---|---|---|---|---|
| WO | WO 2015/086525 | 6/2015 | | |
| WO | WO 2016/050975 | 4/2016 | | |
| WO | WO2016050975 | * 4/2016 | ......... | C07D 487/18 |
| WO | WO 2018/187503 | 10/2018 | | |

OTHER PUBLICATIONS

Tansey & Szymkowski, Drug Discovery Today, vol. 14, Nos. 23/24, Dec. 2009, pp. 1082-1088.
Carneiro et al., J. Sexual Medicine 7, 2010, 7:3823-3834.
Wu et al., JAMA, May 15, 2013, vol. 309, No. 19, pp. 2043-2044.
Hauwermeiren et al., Journal of Clinical Investigation, Jun. 2013, vol. 123, No. 6, pp. 2590-2603.

* cited by examiner

*Primary Examiner* — Jeffrey H Murray
(74) *Attorney, Agent, or Firm* — McDonnell Boehnen Hulbert & Berghoff LLP

(57) ABSTRACT

A compound of formula (I) as defined herein, or a pharmaceutically acceptable salt thereof, being potent modulators of human TNF α activity, are accordingly of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

8 Claims, No Drawings

FUSED PENTACYCLIC IMIDAZOLE DERIVATIVES AS MODULATORS OF TNF ACTIVITY

CROSS-REFERENCE TO RELATED APPLICATIONS

This application is a U.S. national phase application of International Patent Application no. PCT/EP2019/078922 filed Oct. 23, 2019, which claims the benefit of European Patent Application no. 18275165.1 filed Oct. 24, 2018.

The present invention relates to a discrete class of fused pentacyclic imidazole derivatives, and to their use in therapy. More particularly, this invention is concerned with pharmacologically active substituted fused pentacyclic benzimidazole derivatives. These compounds act as modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

The compounds in accordance with the present invention are also potent inhibitors of CD11b expressed on granulocytes in human blood cells which confirms their ability to act as potent TNFα modulators in human cells, as demonstrated by the low $IC_{50}$ value of free compound ("free $IC_{50}$") in the human whole blood assay described herein.

Furthermore, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

WO 2013/186229 relates to substituted benzimidazole derivatives which are modulators of the signalling of TNFα.

WO 2015/086525 relates to fused tricyclic imidazole derivatives which are modulators of the signalling of TNFα.

WO 2016/050975 relates to fused pentacyclic imidazole derivatives which are modulators of the signalling of TNFα.

Copending international patent application PCT/EP2018/060489 relates to a discrete class of fused pentacyclic imidazole derivatives which are modulators of the signalling of TNFα.

The present invention provides a compound of formula (I), or a pharmaceutically acceptable salt thereof:

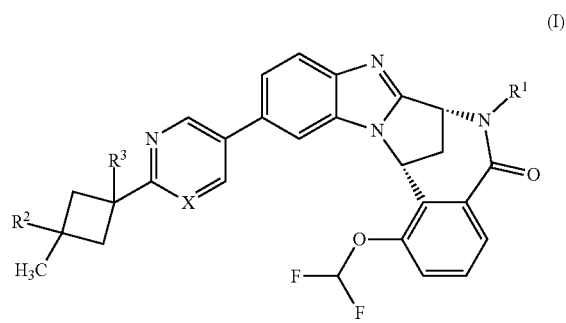

(I)

wherein
X represents N or C—F;
$R^1$ represents hydrogen or methyl (including —$CD_3$);
$R^2$ represents hydroxy or cyano;
$R^3$ represents hydroxy or cyano; and
$R^2$ is different from $R^3$.

The compounds in accordance with the present invention are encompassed within the generic scope of WO 2016/050975. There is, however, no specific disclosure therein of a compound of formula (I) as defined above, or a pharmaceutically acceptable salt thereof.

The present invention also provides a compound of formula (I) as defined above, or a pharmaceutically acceptable salt thereof, for use in therapy.

The present invention also provides a compound of formula (I) as defined above, or a pharmaceutically acceptable salt thereof, for use in the treatment and/or prevention of disorders for which the administration of a modulator of TNFα function is indicated.

In another aspect, the present invention provides a compound of formula (I) as defined above, or a pharmaceutically acceptable salt thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides the use of a compound of formula (I) as defined above, or a pharmaceutically acceptable salt thereof, for the manufacture of a medicament for the treatment and/or prevention of disorders for which the administration of a modulator of TNFα function is indicated.

In another aspect, the present invention provides the use of a compound of formula (I) as defined above, or a pharmaceutically acceptable salt thereof, for the manufacture of a medicament for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above, or a pharmaceutically acceptable salt thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above, or a pharmaceutically acceptable salt thereof.

For use in medicine, the salts of the compounds of formula (I) will be pharmaceutically acceptable salts. Other salts may, however, be useful in the preparation of the compounds of formula (I) or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise.

Suitably, groups $R^2$ and $R^3$ of compounds of formula (I) are arranged cis with respect to one another.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium; D) or $^3H$ (tritium; T) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In a first embodiment, X represents N. In a second embodiment, X represents C—F.

In a first embodiment, $R^1$ represents hydrogen. In a second embodiment, $R^1$ represents methyl. In first aspect of the second embodiment, $R^1$ represents —$CD_3$. In a second aspect of the second embodiment, $R^1$ represents —$CH_3$.

In a first embodiment, $R^2$ represents hydroxy. In a second embodiment, $R^2$ represents cyano.

In a first embodiment, $R^3$ represents hydroxy. In a second embodiment, $R^3$ represents cyano.

Suitably, $R^3$ represents hydroxy, and $R^2$ represents cyano.
Suitably, $R^3$ represents cyano, and $R^2$ represents hydroxy.

Particular sub-classes of compounds in accordance with the present invention include the compounds of formula (IIA) and (IIB), and pharmaceutically acceptable salts thereof:

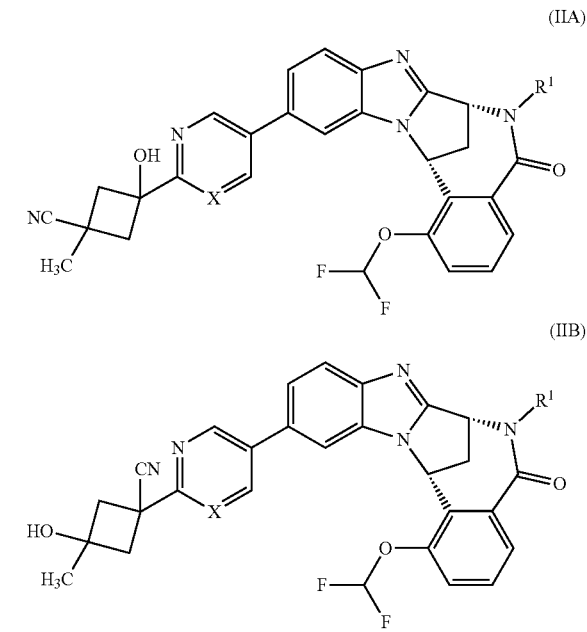

wherein X and $R^1$ are as defined above.

Specific novel compounds in accordance with the present invention include each of the compounds whose preparation is described in the accompanying Examples, and pharmaceutically acceptable salts thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, inflammatory myopathy (including polymyositis, dermatomyositis and inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behcet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy), organ transplant rejection (including kidney allograft rejection), scleritis (including giant cell arteritis scleritis), Takayasu arteritis, hidradenitis suppurativa, pyoderma gangrenosum, sarcoidosis, polymyalgia rheumatic and axial spondyloarthritis.

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis (including iritis) and keratitis.

Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound of formula (I) as defined above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above may be prepared by a process which comprises reacting a compound of formula (III) with a compound of formula (IV):

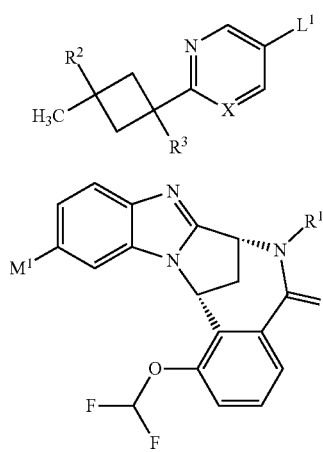

(III)

(IV)

wherein X, $R^1$, $R^2$ and $R^3$ are as defined above, $L^1$ represents a suitable leaving group, $M^1$ represents a boronic acid moiety —$B(OH)_2$ or a cyclic ester thereof formed with an organic diol, e.g. pinacol, 1,3-propane-diol or neopentyl glycol, in the presence of a transition metal catalyst.

The leaving group $L^1$ is typically a halogen atom, e.g. bromo.

The transition metal catalyst of use in the reaction between compounds (III) and (IV) is suitably tris(dibenzylideneacetone)dipalladium(0), or [1,1'-bis(diphenylphosphino)-ferrocene]dichloropalladium(II), or chloro(2-dicyclohexylphosphino-2',4',6'-triisopropyl-1,1'-biphenyl)[2-(2'-amino-1,1'-biphenyl)]palladium(II) (XPhos Pd G2). The transition metal catalyst may typically be utilised in conjunction with 2-dicyclohexylphosphino-2',4',6'-triisopropylbiphenyl (XPhos) or tricyclohexylphosphonium tetrafluoroborate. The reaction is suitably performed in the presence of potassium phosphate or potassium carbonate. The reaction is conveniently carried out at an elevated temperature in a suitable solvent, e.g. a cyclic ether such as 1,4-dioxane, optionally in admixture with water.

The intermediates of formula (IV) above wherein $M^1$ represents a cyclic ester of a boronic acid moiety —$B(OH)_2$ formed with pinacol may be prepared by reacting bis-(pinacolato)diboron with a compound of formula (V):

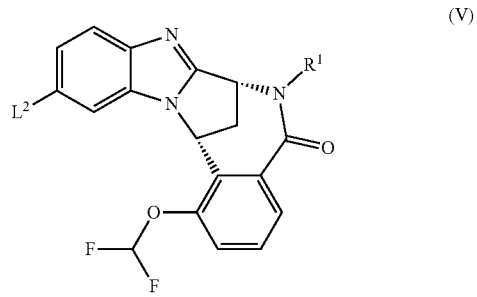

(V)

wherein $L^2$ represents a suitable leaving group; in the presence of a transition metal catalyst.

The leaving group $L^2$ is typically a halogen atom, e.g. chloro.

The transition metal catalyst of use in the reaction between bis(pinacolato)diboron and compound (V) is suitably tris(dibenzylideneacetone)dipalladium(0), which may be utilised in conjunction with 2-dicyclohexylphosphino-2',4',6'-triisopropylbiphenyl (XPhos) or tricyclohexylphosphonium tetrafluoroborate. The reaction is suitably performed in the presence of potassium acetate. The reaction is conveniently carried out at an elevated temperature in a suitable solvent, e.g. a cyclic ether such as 1,4-dioxane.

The intermediates of formula (V) above wherein $R^1$ is methyl may be prepared from the corresponding compound of formula (V) wherein $R^1$ is hydrogen by reaction with a methyl halide, e.g. iodomethane. The methylation reaction is generally performed in the presence of a base, e.g. a silylamide base such as potassium bis(trimethylsilyl)amide. The reaction may conveniently be carried out in a suitable solvent, e.g. a cyclic ether solvent such as tetrahydrofuran.

The intermediate of formula (V) above wherein $R^1$ is hydrogen and $L^2$ represents chloro is specifically disclosed in WO 2016/050975, as also are the intermediates of formula (IV) above wherein $R^1$ is respectively hydrogen or —$CD_3$, and $M^1$ represents 4,4,5,5-tetramethyl-1,3,2-dioxaborolan-2-yl.

Intermediates of formula (III) wherein $R^3$ is hydroxy may be prepared by reacting an intermediate of formula (VI) with an intermediate of formula (VII),

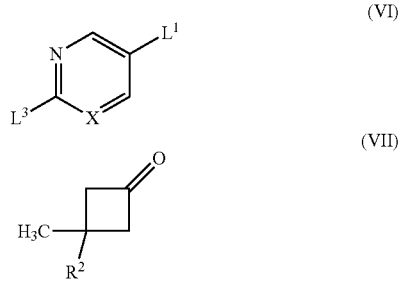

(VI)

(VII)

wherein X, $L^1$ and $R^2$ are as defined above and $L^3$ is a suitable leaving group; in the presence of n-BuLi.

The leaving group $L^3$ is typically a halogen atom e.g. chloro or iodo.

The reaction is conveniently effected in dichloromethane at low temperature according to methods well known to the person skilled in the art.

Intermediates of formula (III) wherein $R^3$ is cyano may be prepared from intermediates of formula (VIII),

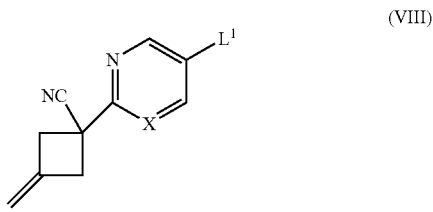

(VIII)

wherein X and $L^1$ are as defined above, by reaction with tetrafluoroboric acid at elevated temperature.

Alternatively, when X represents C—F, intermediate of formula (VIII) may first be oxidized into the corresponding epoxide in the presence of 3-chloroperoxybenzoic acid, in a suitable solvent e.g. dichloromethane, followed by reaction with sodium borohydride in a suitable solvent e.g. ethanol or methanol or a mixture thereof.

Intermediates of formula (VIII) may be prepared by methods analogous to those described in the accompanying Examples, or by standard methods well known from the art.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes give rise to mixtures of stereoisomers, these isomers may be separated by conventional techniques. In particular, where it is desired to obtain a particular enantiomer, this may be produced from a corresponding mixture of enantiomers using any suitable conventional procedure for resolving enantiomers. Thus, for example, diastereomeric derivatives, e.g. salts, may be produced by reaction of a mixture of enantiomers, e.g. a racemate, and an appropriate chiral compound, e.g. a chiral acid or base. The diastereomers may then be separated by any convenient means, for example by crystallisation, and the desired enantiomer recovered, e.g. by treatment with an acid in the instance where the diastereomer is a salt. In another resolution process a racemate may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used where it is desired to obtain a particular geometric isomer. Alternatively the non-desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, compounds of the present invention exhibit an $IC_{50}$ value of 10 nM or better (the skilled person will appreciate that a lower $IC_{50}$ figure denotes a more active compound).

Furthermore, the compounds in accordance with the present invention are potent inhibitors of CD11b expressed on granulocytes in human blood cells, when tested in the human whole blood assay as described herein. When tested in this assay, compounds of the present invention exhibit an $IC_{50}$ for the free compound (herein after referred as "free $IC_{50}$") of 15 nM or less (the skilled person will appreciate that, in such an assay, a lower value of $IC_{50}$ denotes a superior compound, i.e. a compound which displays a greater inhibition of the expression of CD11b on granulocytes and which consequently is a better modulator of TNFα).

Reporter Gene Assay
Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibition of compounds was calculated against TNFα containing DMSO alone (control) and maximum inhibition generated with excess blocking anti-TNFα monoclonal antibody. An inhibition curve was constructed in ActivityBase using a 4 parameter logistic model (XLfit™). The point of inflexion between the fitted minimum and maximum effects of the inhibitor gives the $IC_{50}$ value.

When tested in the reporter gene assay, the compounds of the accompanying Examples were all found to exhibit $IC_{50}$ values of 10 nM or better.

When tested in the reporter gene assay, the compounds of the accompanying Examples exhibit $IC_{50}$ values generally in the range of 0.01 nM to 10 nM.

TNF Human Whole Blood Screening Assay

The compounds according to the Examples were assessed in a human whole blood assay driven by endogenously expressed TNFα by measuring the expression of CD11b on granulocytes in human whole blood challenged with zymosan. Zymosan binds to TLR2 and other receptors, leading to NF-κB signalling which in turn induces the production of pro-inflammatory mediators, including TNFα. In turn, TNFα can stimulate the expression of CD11b on granulocytes.

Compounds were diluted from 10 mM DMSO stocks (final assay concentration of 0.2% DMSO) to generate a 10-point 2.5-fold serial dilution curve (for example, 20,000 nM to 5.3 nM final assay concentration). Diluted compound was preincubated with EDTA anticoagulated human whole blood for 60 minutes at 37° C. prior to stimulation with 1 ug/ml zymosan. After 3 hours stimulation with zymosan, the whole blood was stained with fluorescent labelled anti CD45 and anti CD11b antibodies. The samples were fixed and red blood cells lysed before analysis with a FACS CANTO II.

FACS (Fluoresceence Activated Cell Sorting) analysis was performed with FloJo software. SSC-A (Side Scatter Area of peak) and CD45 signal was used to identify granulocytes, followed by SSC-A and SSC-W (Side Scatter Width of peak) to select single cells. MESF (Molecules of Equivalent Soluble Fluorochrome) beads were used to calibrate the CD11b signal on single cell granulocytes. Activation of CD11b was inhibited in a dose dependent manner by the TNFα inhibitor.

Percentage inhibition of compounds was calculated against TNFα containing DMSO alone (control) and maximum inhibition generated with excess blocking anti-TNFα monoclonal antibody. An inhibition curve was constructed in ActivityBase using a 4 parameter logistic model (XLfit™). The point of inflexion between the fitted minimum and maximum effects of the inhibitor gives the $IC_{50}$ value.

When tested, compounds of the accompanying Examples exhibit $IC_{50}$ values ranging between approximately 50 nM and approximately 300 nM.

Human Blood Binding Assay

The objective of this assay is to determine the fraction unbound in blood of the compounds according to the invention.

Compound according to the present invention is prepared in species specific blood. The blood solution is added to one side of the membrane in an equilibrium dialysis system while buffer (100 mM phosphate buffer pH 7.4) is added to the other side. The system is allowed to reach equilibrium at 37° C. Compound on both sides of the membrane is measured by LC-MS/MS and the fraction of unbound compound is calculated.

Blood is sampled using lithium heparin as the anticoagulant and is used for the assay within 24 hr. Solutions of test compound (1 μM; 0.5% final DMSO concentration) are prepared in human blood that has been diluted 1:1 (v:v) dilution in 100 mM phosphate buffer. The experiment is performed using equilibrium dialysis with the two compartments separated by a semi-permeable membrane. Buffer (100 mM phosphate buffer; pH 7.4) is added to one side of the membrane and the blood solution containing the test compound is added to the other side. After equilibration for 4 hr at 37° C. in an incubator with 5% CO2 and agitation at 300 rpm on an orbital shaker, samples are taken from both sides of the membrane. Samples are matrix matched by addition of either buffer or blood to relevant samples (i.e. buffer added to blood samples and blood is added to buffer samples). Protein is then precipitated from the matrix-matched samples by addition of methanol containing internal standard (200 μL methanol with IS to 100 μL of sample) followed by centrifugation at 4° C. at 2500 rpm for 30 min. Supernatant is then diluted with water prior to analysis. Test compound incubations are performed in duplicate. A control compound, haloperidol, is included in each experiment.

The fraction unbound in blood (Fu) and the percent recovery is measured. Peak area ratio data for all samples are also measured.

When tested, compounds of the accompanying Examples exhibit a fraction unbound in blood, expressed as a percentage, ranging between approximately 1% and approximately 7%.

A calculated $IC_{50}$ for the free compound (herein referred to as "free $IC_{50}$") that takes into account the extent of fraction unbound in blood was determined by multiplying the $IC_{50}$ generated from the first assay (human whole blood screening assay) by the unbound fraction (Fu), generated from the second assay (human blood binding assay).

When tested, the compounds of the accompanying Examples exhibit values of free $IC_{50}$ in the human whole blood assay of 15 nM or better. It will be understood by the person skilled in the art that a "better" value of $IC_{50}$ is a lower value of $IC_{50}$.

Specifically, the compound of Example 2 exhibits a free $IC_{50}$ value of approximately 12 nM; the compound of Examples 1 and 3 exhibits a free $IC_{50}$ value of approximately 6 nM; the compound of Example 5 exhibits a free $IC_{50}$ value of approximately 5 nM; and Examples 4, 6 and 7 all exhibit a free $IC_{50}$ value better than 4 nM.

The following Examples illustrate the preparation of compounds according to the invention.

EXAMPLES

Abbreviations

| | |
|---|---|
| DCM: dichloromethane | EtOAc: ethyl acetate |
| MeOH: methanol | THF: tetrahydrofuran |
| DMSO: dimethyl sulfoxide | EtOH: Ethanol |
| MeCN: acetonitrile | h: hour |
| TBME: Methyl tert-butyl ether | RT: retention time |
| XPhos: 2-dicyclohexylphosphino-2', 4',6'-triisopropylbiphenyl | |
| r.t.: room temperature | |
| M: mass | |

| | |
|---|---|
| HPLC: | High Performance Liquid Chromatography |
| LCMS: | Liquid Chromatography Mass Spectrometry |
| ES+: | Electrospray Positive Ionisation |

Nomenclature

IUPAC names of all the Intermediates and Examples described herein were generated using Pipeline Pilot (version 2018) which uses OEMMetachem software version 1.4.5. provided by OpenEye Scientific.

Analytical Conditions

All NMR spectra were obtained at 250 MHz, 300 MHz, 400 MHz or 500 MHz.

All reactions involving air- or moisture-sensitive reagents were performed under a nitrogen atmosphere using dried solvents and glassware.

LCMS Data Determination

Method 1

Method 1: Performed using an Agilent 1200RR-6140 LC-MS system, with an Agilent binary pump and Agilent DAD (230-400 nm) module. 6140 mass detection (ES) 100-1000 m/z.

Column: XBridge C18, 2.1×20 mm, 2.5 μm

Mobile Phase A: 10 mM Ammonium Formate in water+ 0.1% Ammonia Solution

Mobile Phase B: Acetonitrile+5% water+0.1% Ammonia Solution

| Gradient: | Time | A % | B % |
|---|---|---|---|
| | 0.00 | 95.10 | 5.00 |
| | 4.00 | 5.00 | 95.00 |
| | 5.00 | 5.00 | 95.00 |
| | 5.10 | 95.00 | 5.00 |
| Flow: | 1 mL/min | | |
| Run Time: | 6 min | | |

Method 2

Method 2: Crude system 2 (basic)—Performed using an Agilent 1260-6120 LC-MS system, with an Agilent binary pump and Agilent DAD (240-400 nm) module. 6120 mass detection (ES) 120-1000 m/z.

Column: XBridge C18, 2.1×20 mm, 2.5 μm

Mobile Phase A: 10 mM Ammonium Formate in water+ 0.1% Ammonia Solution

Mobile Phase B: Acetonitrile+5% water+0.1% Ammonia Solution

| Gradient: | Time | A % | B % |
|---|---|---|---|
| | 0.00 | 95.00 | 5.00 |
| | 1.50 | 5.00 | 95.00 |
| | 2.25 | 5.00 | 95.00 |
| | 2.50 | 95.00 | 5.00 |
| Flow Rate: | 1 mL/min | | |
| Run Time: | 3.5 min | | |

Method 3

Method 3: Crude system 2 (basic)—Performed using an Agilent 1260-6120 LC-MS system, with an Agilent binary pump and Agilent DAD (240-400 nm) module. 6120 mass detection (ES) 120-1000 m/z.

Column: XBridge C18, 2.1×20 mm, 2.5 μm

Mobile Phase A: 10 mM Ammonium Formate in water+ 0.1% Ammonia Solution

Mobile Phase B: Acetonitrile+5% water+0.1% Ammonia Solution

Gradient:

| Time | A % | B % |
|---|---|---|
| 0.00 | 95.00 | 5.00 |
| 4.00 | 5.00 | 95.00 |
| 5.00 | 5.00 | 95.00 |
| 5.00 | 95.00 | 5.00 |
| Flow Rate: | | 1 mL/min |
| Run Time: | | 6 min |

Method 4

Waters UPLC-SQD apparatus, ionization: electrospray in positive and/or negative mode (ES+/−), chromatographic conditions: column: Acquity CSH C18 1.7 μm-2.1×50 mm, solvents: A: H2O (0.1% formic acid) B: CH$_3$CN (0.1% formic acid), column temperature: 45° C., flow rate: 1.0 ml/min, gradient (2.5 min): from 5 to 100% of B.

Intermediate 1

(1R,11R)-5-chloro-18-(difluoromethoxy)-12-methyl-2,9,12-triazapentacyclo[9.8.1.0<sup>2,10</sup>.0<sup>3,8</sup>.0<sup>14,19</sup>]icosa-3(8),4,6,9,14(19),15,17-heptaen-13-one

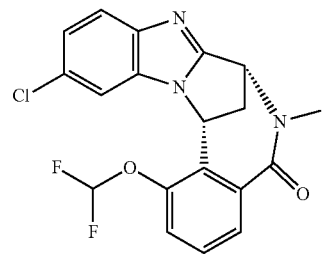 [SMILES: CN1C(=O)c2cccc(OC(F)F)c2[C@H]2C[C@@H]1c1nc3ccc(Cl)cc3n12]

To a solution of (7R,14R)-11-chloro-1-(difluoromethoxy)-6,7-dihydro-7,14-methanobenzimidazo[1,2-b][2,5]benzodiazocin-5(14I)-one (WO 2016/050975, Example 11) (10 g, 26.6 mmol) in dry THF (135 mL), cooled to −78° C. under nitrogen, was added potassium bis(trimethylsilyl)amide (1M in THF, 30 mL, 30 mmol) dropwise over 15 minutes. The resulting mixture was stirred at −78° C. for 1 h prior to the addition of iodomethane (2.5 mL, 40 mmol) dropwise over 5 minutes. The reaction mixture was stirred at −78° C. for 1 h, then allowed to warm slowly to ambient temperature overnight. The reaction mixture was poured into saturated aqueous ammonium chloride solution (600 mL) and extracted with EtOAc (2×800 mL). The organic extracts were dried (Na$_2$SO$_4$), filtered and concentrated in vacuo. Purification by flash chromatography on silica (elution with 5% MeOH/DCM) afforded the title compound (9.12 g, 88%) as a beige solid.

δ$_H$ (300 MHz, DMSO-d$_6$) 8.33-8.21 (m, 1H), 7.87-7.33 (m, 5H), 7.22 (dd, J 8.7, 2.1 Hz, 1H), 6.23 (d, J 7.1 Hz, 1H), 5.22 (d, J 7.1 Hz, 1H), 3.55-3.41 (m, 1H), 3.33 (s, 3H), 2.81 (d, J 13.8 Hz, 1H). LCMS (ES+) [M+H]$^+$ 390.0, RT 1.10 minutes (Method 2).

Intermediate 2

(1R,11R)-18-(difluoromethoxy)-12-methyl-5-(4,4,5,5-tetramethyl-1,3,2-dioxaborolan-2-yl)-2,9,12-triazapentacyclo[9.8.1.02,10.03,8.014,19]icosa-3(8),4,6,9,14(19),15,17-heptaen-13-one

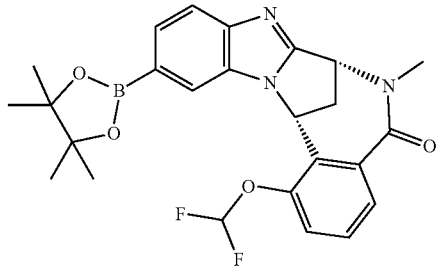 [SMILES: CN1C(=O)c2cccc(OC(F)F)c2[C@H]2C[C@@H]1c1nc3ccc(B4OC(C)(C)C(C)(C)O4)cc3n12]

Intermediate 1 (4 g, 10.3 mmol) in 1,4-dioxane (42 mL) was treated with bis(pinacolato)diboron (3.9 g, 15 mmol) and potassium acetate (3 g, 30.6 mmol). The reaction mixture was degassed and flushed with nitrogen. Tris(dibenzylideneacetone)dipalladium(0) (484 mg, 0.51 mmol), and tricyclohexylphosphonium tetrafluoroborate (390 mg, 1.03 mmol) was added and the reaction mixture was degassed and nitrogen flushed before heating overnight at 140° C. Further bis(pinacolato)diboron (2.6 g, 10.3 mmol) was added and the reaction mixture was heated at 140° C. for 24 h. The reaction mixture was partitioned between EtOAc and brine, the organic phase was separated, concentrated in vacuo and purified by flash column chromatography on silica (gradient elution with EtOAc/MeOH 0 to 10%) to afford the title compound (2.5 g, 50%) as a white solid.

LCMS (ES+) [M+H]$^+$ 482, RT 2.40 minutes (Method 3).

Intermediate 3

3-(5-bromopyrimidin-2-yl)-3-hydroxy-1-methylcyclobutane-1-carbonitrile

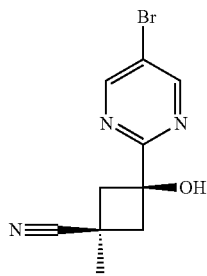

1-methyl-3-oxo-cyclobutanecarbonitrile (2.0 g, 18.3 mmol) and 5-bromo-2-iodo-pyrimidine (6 g, 21.0 mmol), both available commercially, were dissolved in DCM (100 mL). The mixture was cooled to −78° C. before the dropwise addition of n-butyllithium (8.4 mL, 21 mmol, 2.5 mol/L) The mixture was stirred at −78° C. for one hour before slowly warming up to r.t. and stirred for additional hour. The mixture was filtered through phase separator, washed with DCM, concentrated in vacuo. The crude product was s purified by flash column chromatography on silica (gradient elution with 0-10% EtOAc/hexane) to give the major undesired isomer, 700 mg, and mixed fractions (1.7 g) containing both isomers with rough ratio of 1:1. The mixed fraction were combined and purified by preparative LC to afford title compound as a yellow solid (700 mg, 10%)

LCMS (ES+) [M+H]$^+$ 250/270, RT 0.90 minutes (Method 3).

Intermediate 4

(1R,11R)-18-(difluoromethoxy)-6-fluoro-5-(4,4,5,5-tetramethyl-1,3,2-dioxaborolan-2-yl)-2,9,12-triazapentacyclo[9.8.1.02,10.03,8.014,19]icosa-3(8),4,6,9,14(19),15,17-heptaen-13-one

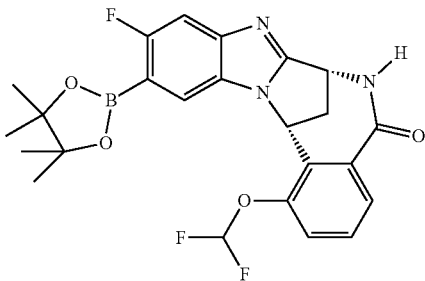 [SMILES: CC1(C)OB(c2cc3c(cc2F)nc2n3[C@@H]3C[C@H]2NC(=O)c2cccc(OC(F)F)c23)OC1(C)C]

(7R,14R)-11-chloro-1-(difluoromethoxy)-10-fluoro-6,7-dihydro-7,14-methanobenzimidazo[1,2-b][2,5]benzodiazocin-5(14H)-one (Example 10 of WO 2016/050975) (150 mg, 0.38 mmol) in 1,4-dioxane (1.3 mL, 15 mmol) was added to bis(pinacolato)diboron (145.1 mg, 0.57 mmol), and potassium acetate (112 mg, 1.14 mmol), tricyclohexylphosphonium tetrafluoroborate (14 mg, 0.038 mmol) and tris(dibenzylideneacetone)dipalladium(0) (18 mg, 0.019 mmol) were added. The reaction mixture was degassed for 10 mins before heating up to 140° C. in a seal tube for 3 hours in the microwave. After this time water and EtOAc was added to the reaction mixture. The two phases were separated and the aqueous layer was extracted with EtOAc. The combined organic layers were filtered through a phase separator and the solvent was evaporated. The residue was purified by flash column chromatography on silica (gradient elution with EtOAc/isohexane from 0 to 100% and then DCM/MeOH from 0 to 15%. The fractions containing the product were combined and the solvent evaporated to afford the title compound as a grey solid (145 mg, 79%).

LCMS (ES+) [M+H]$^+$ 486, RT 1.90 minutes (Method 3).

Intermediate 5

3-(5-bromo-3-fluoropyridin-2-yl)-3-hydroxy-1-methylcyclobutane-1-carbonitrile

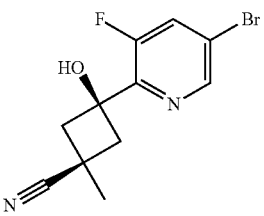 [SMILES: C[C@]1(C#N)C[C@](O)(c2ncc(Br)cc2F)C1]

A solution of n-butyllithium (2.5 M in hexane, 12.54 mL, 31.3 mmol) was added dropwise to a solution of 2,5-dibromo-3-fluoropyridine (7.99 g, 31.3 mmol) in toluene (200 mL) at −70° C. and after addition the reaction mixture was stirred at −70° C. over 1 h. A solution of 1-methyl-3-oxocyclobutanecarbonitrile (3.00 g, 26.1 mmol) in toluene (50 mL) was added dropwise to the reaction mixture at −70° C. and the resulting solution was then stirred over 2 h at −70° C.

The reaction mixture was then allowed to warm up to 0° C. and a saturated solution of ammonium chloride (50 mL) was added at 0° C. The resulting mixture was extracted with EtOAc (2×100 mL) and the combined organic phases were washed with brine, dried over MgSO4, filtered and concentrated in vacuo. The residue was purified by flash column chromatography on silica (gradient elution with MeOH/DCM 0-2%) to afford the title compound (857 mg, 11.5%).

$^1$H NMR (400 MHz, DMSO-d$_6$) δ: 1.29 (s, 3H), 2.6 (d, J=13.3 Hz, 1H), 2.89 (dd, J=1.8 & 13.3 Hz, 1H), 6.21 (s, 1H), 8.17 (dd, J=1.8 & 10.2 Hz, 1H), 8.53 (t, J=1.8 Hz, 1H).

Intermediate 6

3-methylidene-1-(morpholine-4-carboximidoylcy-clobutane-1-carbonitrile

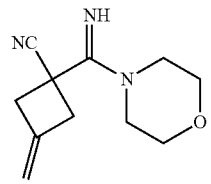

3-methylenecyclobutanecarbonitrile (8 g, 83.3 mmol, was dissolved in tetrahydrofuran (100 mL) lithium diisopropylamide (46 mL, 92 mmol, 2.0 mol/L) was added dropwise at −78° C. The mixture was stirred at −78° C. for 1 hour before adding the solution of morpholine-4-carbonitrile (9.4 mL, 92 mmol) in THF (20 mL) dropwise. The mixture was stirred at −78° C. for 1 additional hour. The reaction was quenched with saturated NH$_4$Cl solution and extracted twice with TBME. The organics were combined and concentrated. The crude material was purified by flash column chromatography on silica (gradient elution with 0-20% MeOH/DCM) to give the title compound (8.0 g, 47%).

LCMS (ES+) [M+H]$^+$ 206, RT 0.68 minutes (Method 3).

Intermediate 7

1-(5-bromopyrimidin-2-yl)-3-methylidenecyclobu-tane-1-carbonitrile

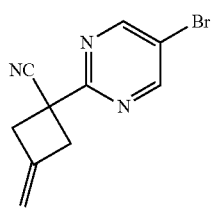

5-bromo-1,2,3-triazine available commercially (1.30 g, 8.13 mmol) was suspended in MeCN (5 mL) and cooled in an ice bath. A solution of Intermediate 6 (1.83 g, 8.92 mmol) in MeCN (10 mL) was then added dropwise. After stirring for 10 min the ice bath was removed and the reaction heated to 45° C. overnight. The mixture was reduced under vacuum and the residue purified by flash column chromatography on silica (gradient elution with 0-25% EtOAc/isohexane). Relevant fractions combined and concentrated to give the title compound as a yellow oil which solidified upon standing (375 mg, 18.5%).

LCMS (ES+) [M+H]$^+$ 250/252, RT 1.99 minutes (Method 3).

Intermediate 8

1-(5-bromopyrimidin-2-yl)-3-hydroxy-3-methylcy-clobutane-1-carbonitrile

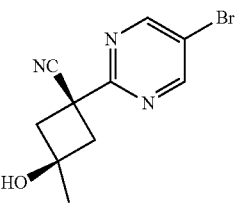

Intermediate 7 (375 mg, 1.50 mmol) in tetrafluoroboric acid (2.5 mL, 19 mmol) was heated to 70° C. for 6 hr before cooling. The reaction was quenched by addition of saturated sodium bicarbonate solution. EtOAc was then added and the layers were separated and the aqueous layer again extracted with EtOAc. The combined organic phase was dried, filtered and reduced under vacuum. The residue was purified flash column chromatography on silica (gradient elution with 20-50% EtOAc/isohexane). The relevant fractions were combined and concentrated under vacuum to afford product as a mixture of isomers. These were then separated by preparative HPLC to afford title compound as a white solid (110 mg, 27%).

LCMS (ES+) [M+H]$^+$ 268/270, RT 0.93 minutes (Method 3).

$^1$H NMR (400 MHz, DMSO-d$_6$) δ 9.10 (s, 2H), 2.95-2.85 (m, 2H), 2.84-2.75 (m, 2H), 1.21 (s, 3H).

Intermediate 9

1-(5-bromo-3-fluoropyridin-2-yl)-3-methylidenecy-clobutane-1-carbonitrile

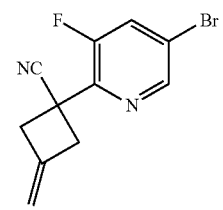

In a 1 litre 3-necked round bottom flask, under nitrogen, were combined 5-bromo-2,3-difluoropyridine (25.0 g, 126 mmol) and 3-methylenecyclobutanecarbonitrile (16 mL, 152 mmol) in anhydrous toluene (250 mL). The solution was cooled to 0° c. (ice/salt bath). Then sodium bis(trimethylsilyl)amide (242 mL, 145 mmol) was added via a dropping funnel. During the addition the temperature rose to 12° C. for a short time. When the addition was complete the reaction was stirred for 45 minutes at 0° C. The reaction mixture was poured into 1 M citric acid (200 mL), layers separated and the aqueous layer extracted with EtOAc (2×250 mL). The combined organics were passed through a phase separator, filtered and concentrated in vacuo to give a brown oil. This was purified with flash column chromatography on silica (gradient elution with 0-20% EtOAc/isohexane to afford title compound as a white solid (25.2 g, 75%)

LCMS (ES+) [M+H]+ 267/269, RT 1.09 minutes (Method 2).

Intermediate 10

5-(5-bromo-3-fluoropyridin-2-yl)-1-oxaspiro[2.3]hexane-5-carbonitrile

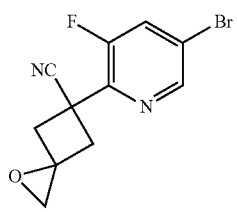 [SMILES: N#CC1(c2ncc(Br)cc2F)CC2(CO2)C1]

3-chloroperoxybenzoic acid (2.69 g, 12.0 mmol) was added to a solution of Intermediate 9 (1.50 g, 5.62 mmol) in DCM (60 mL) and stirred at r.t. overnight. Reaction was quenched with sat. aq. Na2S2O5 solution, diluted with DCM and the layers separated. The organic layer was washed twice with sat. bicarb and then water before concentrating under vacuum. This residue was purified with flash column chromatography on silica (gradient elution with 10-30% EtOAc/isohexane). The relevant fractions were combined and concentrated under vacuum to give an off-white solid (1.10 g, 69%).

LCMS (ES+) [M+H]+ 283/285, 1.53 minutes (Method 3).

Intermediate 11

1-(5-bromo-3-fluoropyridin-2-yl)-3-hydroxy-3-methylcyclobutane-1-carbonitrile

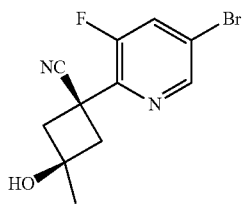

Intermediate 10 (900 mg, 3.18 mmol) was dissolved in anhydrous EtOH (30 mL), stirred for 10 min. Anhydrous MeOH (5 mL) was then added to aid solubility followed by sodium borohydride (425 mg, 11.1 mmol). After 6.5 hr, the reaction was quenched by partitioning between sat. aq. ammonium chloride and EtOAc. Layers were separated and the aqueous layer was further extracted with EtOAc. The combined organic phase was washed with brine and then dried, filtered and reduced under vacuum. The crude residue was purified with flash column chromatography on silica (gradient elution with 30-45% EtOAc/isohexane). Relevant fractions were combined and concentrated under vacuum to afford product as a mixture of isomers. These were separated by preparative HPLC to afford Intermediate 11 as a white solid (52 mg, 6%) LCMS (ES+) [M+H]+ 285/287, RT 1.28 minutes. (Method 3).

$^1$H NMR (400 MHz, DMSO-$d_6$) δ 8.69-8.62 (m, 1H), 8.36 (dd, J=10.0, 1.9 Hz, 1H), 5.54 (s, 1H), 2.97 (d, J=12.7 Hz, 2H), 2.80 (d, J=12.7 Hz, 2H), 1.05 (s, 3H).

Example 1

3-[5-[(1R,11R)-18-(difluoromethoxy)-13-oxo-12-(trideuteriomethyl)-2,9,12-triazapentacyclo[9.8.1.02,10.03,8.014,19]icosa-3(8),4,6,9,14(19),15,17-heptaen-5-yl]pyrimidin-2-yl]-3-hydroxy-1-methylcyclobutane-1-carbonitrile

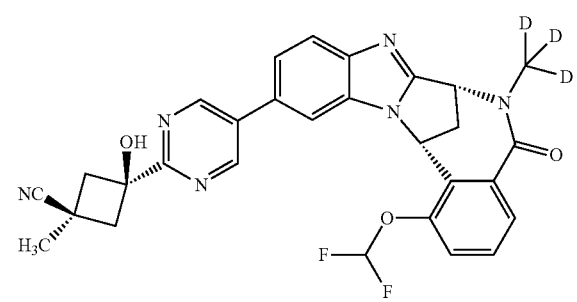 [SMILES: [2H]C([2H])([2H])N1C(=O)c2cccc(OC(F)F)c2[C@H]2C[C@@H]1c1nc3ccc(-c4cnc([C@]5(O)C[C@@](C)(C#N)C5)nc4)cc3n12]

(7R,14R)-11-chloro-1-(difluoromethoxy)-6-(trideutero)methyl-6,7-dihydro-7,14-methanobenzimidazo[1,2-b][2,5]benzodiazocin-5(14H)-one (Intermediate 159 of WO 2016/050975) (700 mg, 1.44 mmol), Intermediate 3 (461 mg, 1.72 mmol), potassium phosphate tribasic (1252 mg, 5.78 mmol) and tricyclohexylphosphonium tetrafluoroborate (66 mg, 0.174 mmol) were suspended in a mixture of 1,4-dioxane (15 mL, 175 mmol) and water (2 mL). The mixture was degassed/nitrogen-purged 3 times before addition of tris(dibenzylideneacetone)dipalladium(0) (70 mg, 0.074 mmol). The mixture was further degassed/nitrogen-purged and heated in a microwave at 110° C. for 2.5 hours. The mixture was then diluted with water and twice extracted with EtOAc. The organics were combined, dried and concentrated in vacuo. The crude product was purified by flash column chromatography on silica (gradient elution 0-100% EtOAc/isohexane and 0-10% MeOH/DCM to give the title compound (343 mg, 31%).

LCMS (ES+) [M+H]+ 546, RT 1.97 minutes (Method 1).

$^1$H NMR (400 MHz, DMSO-$d_6$) δ 9.11 (s, 2H), 8.28 (dd, J=6.1, 3.3 Hz, 1H), 7.83-7.74 (m, 2H), 7.69 (t, J=73.0 Hz, 1H), 7.64 (dd, J=8.5, 1.8 Hz, 1H), 7.55-7.46 (m, 2H), 6.32 (d, J=7.1 Hz, 1H), 6.16 (s, 1H), 5.26 (d, J=7.1 Hz, 1H), 3.53 (dt, J=14.1, 7.2 Hz, 1H), 2.96-2.86 (m, 2H), 2.85 (d, J=13.7 Hz, 1H), 2.81-2.72 (m, 2H), 1.45 (s, 3H).

Example 2

3-[5-[(1R,11R)-18-(difluoromethoxy)-13-oxo-2,9,12-triazapentacyclo[9.8.1.02,10.03,8.014,19]icosa-3(8),4,6,9,14(19),15,17-heptaen-5-yl]pyrimidin-2-yl]-3-hydroxy-1-methylcyclobutane-1-carbonitrile

Example 3

3-[5-[(1R,11R)-18-(difluoromethoxy)-6-fluoro-13-oxo-2,9,12-triazapentacyclo[9.8.1.02,10.03,8.014,19]icosa-3(8),4,6,9,14(19),15,17-heptaen-5-yl]pyrimidin-2-yl]-3-hydroxy-1-methylcyclobutane-1-carbonitrile

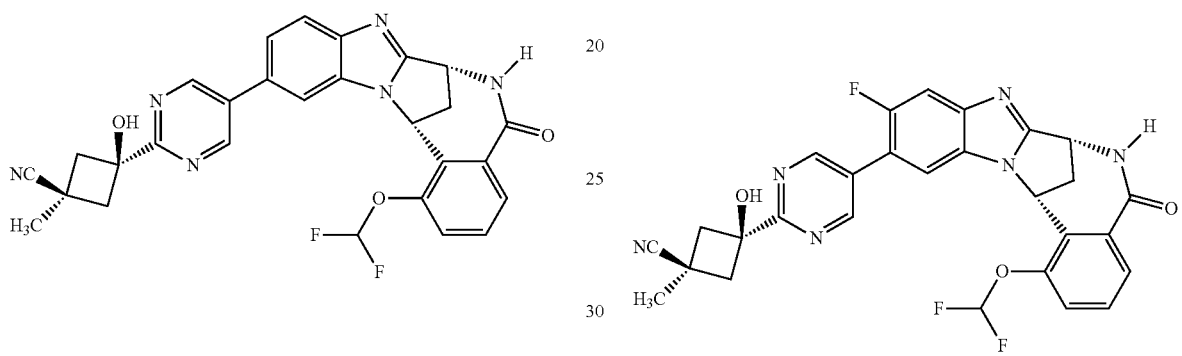

A flame-dried three-necked flask under nitrogen was charged with (6R,12R)-2-chloro-11-(difluoromethoxy)-7,12-dihydro-6H-6,12-methanobenzimidazo[2,1-c][1,4]benzodiazepine (Example 11 of WO 2016/050975 (750 mg, 1.996 mmol)), XPhos(PiAllyl) precatalyst (67 mg, 0.099 mmol), potassium acetate (494 mg, 4.98 mmol) and bis(pinacolato)diboron (532 mg, 2.10 mmol) before it was evacuated and backfilled with nitrogen three times. Then, 1,4-dioxane (4 mL) was added and the mixture was stirred at 100° C. After 3.5 hours, a solution of Intermediate 3 (589 mg, 2.20 mmol) in dry 1,4-dioxane (2 mL) was added followed by aqueous solution of potassium phosphate tribasic (1.5 mL, 3.0 mmol). Stirring at 100° C. was continued for 19 hours before the mixture was cooled down to r.t. poured into brine (100 mL), diluted with EtOAc (100 mL) and partitioned. The aqueous washings were re-extracted with EtOAc (100 mL). The combined organic extracts were dried over $Na_2SO_4$, filtered and concentrated in vacuo. Purification by flash column chromatography on silica (gradient elution with MeOH in DCM (0 to 5%), followed by trituration of the product in Et2O to afford the title compound as a tan solid (511 mg, 49%).

$^1$H NMR (400 MHz, DMSO-$d_6$) δ 9.16 (d, J=6.8 Hz, 1H), 9.11 (s, 2H), 8.23 (dd, J=5.7, 3.8 Hz, 1H), 7.81-7.73 (m, 2H), 7.70 (t, J=73 Hz, 1H), 7.63 (dd, J=8.5, 1.8 Hz, 1H), 7.55-7.46 (m, 2H), 6.38 (d, J=7.0 Hz, 1H), 6.15 (s, 1H), 4.91 (t, J=6.8 Hz, 1H), 3.50 (dt, J=13.6, 7.1 Hz, 1H), 2.96-2.87 (m, 2H), 2.81-2.72 (m, 3H), 1.45 (s, 3H)

LCMS (ES+) [M+H]$^+$ 529, RT 1.45 minutes (Method 3)

Intermediate 4 (910 mg, 1.69 mmol), Intermediate 3 (500 mg, 1.87 mmol), potassium phosphate tribasic (1.10 g, 5.08 mmol) and tricyclohexylphosphonium tetrafluoroborate (65 mg 0.171 mmol) were suspended in 1,4-dioxane (20 mL) and water (5 mL) added. The reaction was degassed with three cycles of vacuum and nitrogen before the addition of tris(dibenzylideneacetone)dipalladium(0) (80 mg 0.085 mmol). The reaction was again degassed/refilled and heated to 100° C. for 4.5 hr before being allowed to cool to r.t. O/N. The reaction was partitioned between brine and EtOAc and the layers separated. The organic layer was removed and the aqueous further extracted with EtOAc. The combined organic phase was dried, filtered and reduced under vacuum. The residue was triturated in DCM and filtered. Material was purified by flash column chromatography on silica (gradient elution with 0-20% MeOH/DCM) and the relevant fractions combined and concentrated to give the title compound as a pale yellow solid (465 mg, 50%).

$^1$H NMR (400 MHz, DMSO-$d_6$) δ 9.17 (d, J=6.9 Hz, 1H), 9.01 (d, J=1.7 Hz, 2H), 8.27-8.20 (m, 1H), 7.69 (d, J=11.4 Hz, 1H), 7.62 (t, J=73.0 Hz, 1H), 7.57 (d, J=6.8 Hz, 1H), 7.54-7.48 (m, 2H), 6.36 (d, J=7.1 Hz, 1H), 6.19 (s, 1H), 4.92 (t, J=6.8 Hz, 1H), 3.55-3.45 (m, 1H), 2.92 (d, J=13.5 Hz, 2H), 2.82-2.70 (m, 3H), 1.46 (s, 3H).

LCMS (ES+) [M+H]$^+$ 547, 1.74 minutes (Method 1).

Example 4

3-[5-[(1R,11R)-18-(difluoromethoxy)-12-methyl-13-oxo-2,9,12-triazapentacyclo[9.8.1.02,10.03,8.014,19]icosa-3,5,7,9,14(19),15,17-heptaen-5-yl]-3-fluoropyridin-2-yl]-3-hydroxy-1-methylcyclobutane-1-carbonitrile

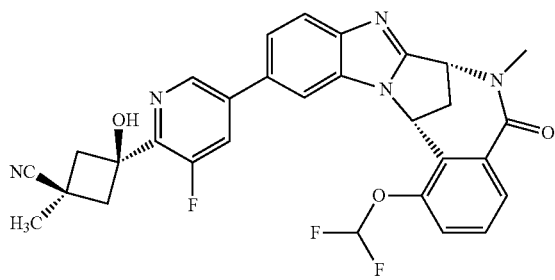

A solution of K₃PO₄ (521 mg, 2.38 mmol) in water (3.75 mL) is added to a mixture of Intermediate 5 (226 mg, 794 μmol) and Intermediate 2 (382 mg, 793 μmol) in 1,4-dioxane (15 mL). Once argon was bubbled through this solution, [bis(diphenylphosphino)ferrocene]-dichloropalladium(II) (30 mg, 40 μmol) was added. The resulting reaction mixture was heated at reflux for 4 h, then was cooled down to room temperature and poured into water (50 mL). This solution was extracted with EtOAc (3×50 mL). The combined organic phases were washed with water (2×50 mL), dried over MgSO4, filtered and concentrated in vacuo. The residue as purified by flash column chromatography on silica (gradient elution with MeOH/DCM 0-5%) to afford the title compound (192 mg, 43%) as a beige solid.

LCMS (ES+) [M+H]⁺ 560, RT 1.28 minutes.

¹H NMR (400 MHz, DMSO-d₆) δ: 1.33 (s, 3H), 2.78 to 2.85 (m, 3H), 2.96 (broad d, J=12.2 Hz, 2H), 3.36 (s, 3H), 3.52 (m, 1H), 5.24 (d, J=7.2 Hz, 1H), 6.16 (s, 1H), 6.30 (d, J=7.2 Hz, 1H), 7.47 to 7.52 (m, 2H), 7.60 (dd, J=1.7 & 8.5 Hz, 1H), 7.68 (t, J=73.3 Hz, 1H), 7.75 (m, 2H), 7.95 (dd, J=2.0 & 12.0 Hz, 1H), 8.27 (m, 1H), 8.65 (d, J=2.0 Hz, 1H).

Example 5

3-[5-[(1R,11R)-18-(difluoromethoxy)-13-oxo-2,9,12-triazapentacyclo[9.8.1.02,10.03,8.014,19]icosa-3,5,7,9,14(19),15,17-heptaen-5-yl]-3-fluoropyridin-2-yl]-3-hydroxy-1-methylcyclobutane-1-carbonitrile

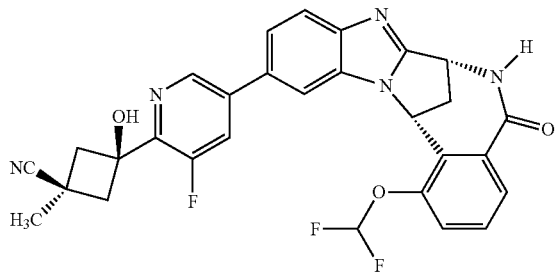

A solution of K₃PO₄ (535 mg, 2.45 mmol) in water (2.5 mL) is added to a mixture of intermediate 5 (232.5 mg, 815.4 μmol) and (7R,14R)-1-(difluoromethoxy)-11-(4,4,5,5-tetramethyl-1,3,2-dioxaborolan-2-yl)-6,7-dihydro-7,14-methanobenzimidazo[1,2-b][2,5]benzodiazocin-5(14H)-one (Intermediate 171 of WO 2016/050975) (381 mg, 815.4 μmol) in 1,4-dioxane (10 mL). Once argon was bubbled through this solution, [bis(diphenylphosphino)ferrocene]-dichloropalladium(II) (31.4 mg, 40.8 μmol) was added. The resulting reaction mixture was heated at reflux for 4 hr, then was cooled down to room temperature and poured into water (50 mL). This solution was extracted with EtOAc (3×50 mL). The combined organic phases were washed with water (2×50 mL), dried over MgSO4, filtered and concentrated in vacuo. The residue was purified by flash chromatography (MeOH/DCM 0-5%) to afford the title compound (67 mg, 15%) as a beige solid.

LCMS (ES+)[M+H]⁺ 546, RT 1.21 minutes (Method 4).

¹H NMR (400 MHz, DMSO-d₆) δ: 1.34 (s, 3H), 2.75 (d, J=13.4 Hz, 1H), 2.80 (broad d, J=13.4 Hz, 2H), 2.96 (broad d, J=13.4 Hz, 2H), 3.49 (m, 1H), 4.89 (t, J=6.9 Hz, 1H), 6.16 (s, 1H), 6.36 (d, J=7.2 Hz, 1H), 7.48 to 7.53 (m, 2H), 7.58 (dd, J=1.8 & 8.6 Hz, 1H), 7.68 (t, J=73.3 Hz, 1H), 7.73 (m, 2H), 7.94 (dd, J=1.8 & 11.9 Hz, 1H), 8.23 (m, 1H), 8.65 (t, J=1.8 Hz, 1H), 9.13 (d, J=6.9 Hz, 1H).

Example 6

1-[5-[(1R,11R)-18-(difluoromethoxy)-12-methyl-13-oxo-2,9,12-triazapentacyclo[9.8.1.02,10.03,8.014,19]icosa-3(8),4,6,9,14(19),15,17-heptaen-5-yl]pyrimidin-2-yl]-3-hydroxy-3-methylcyclobutane-1-carbonitrile

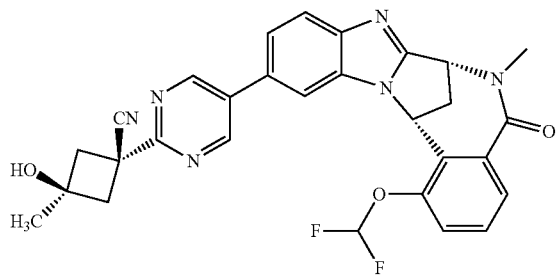 [SMILES: C[C@]1(C#N)C[C@](O)(c2ncc(-c3ccc4nc5n(c4c3)[C@@H]3C[C@H]5NC(=O)c4cccc(OC(F)F)c43)cn2)C1]

Intermediate 2 (140 mg, 0.29 mmol), Intermediate 8 (85 mg, 0.32 mmol), potassium phosphate tribasic (185 mg, 0.85 mmol) and tricyclohexylphosphonium tetrafluoroborate (11 mg, 0.029 mmol) were dissolved in 1,4-dioxane (5 mL) and water (1 mL) added. The reaction was degassed with three cycles of vacuum and nitrogen before the addition of tris(dibenzylideneacetone)dipalladium(0) (14 mg, 0.015 mmol). The reaction was again degassed/refilled with nitrogen and heated to 100° C. for 5 hr before being allowed to cool to r.t. overnight. The reaction mixture was diluted with DCM and water, passed through a phase separator and the organic phase reduced under vacuum. Purified with flash column chromatography on silica (gradient elution with 50-100% EtOAc/isohexane and then 0-10% MeOH/DCM). Desired fractions combined and concentrated under vacuum to afford title compound as a white solid (56 mg, 36%).

LCMS (ES+) [M+H]⁺ 543, RT 1.67 minutes (Method 1).

¹H NMR (400 MHz, DMSO-d₆) δ 9.16 (s, 2H), 8.34-8.21 (m, 1H), 7.83-7.74 (m, 2H), 7.71-7.63 (m, 1H), 7.70 (t, J=73.6 Hz, 1H), 7.54-7.47 (m, 2H), 6.32 (d, J=7.1 Hz, 1H), 5.52 (s, 1H), 5.27 (d, J=7.1 Hz, 1H), 3.61-3.47 (m, 1H), 3.37 (s, 3H), 3.05-2.91 (m, 2H), 2.89-2.79 (m, 3H), 1.24 (s, 3H)

Example 7

1-[5-[(1R,11R)-18-(difluoromethoxy)-12-methyl-13-oxo-2,9,12-triazapentacyclo[9.8.1.02,10.03,8.014,19]icosa-3(8),4,6,9,14(19),15,17-heptaen-5-yl]-3-fluoropyridin-2-yl]-3-hydroxy-3-methylcyclobutane-1-carbonitrile

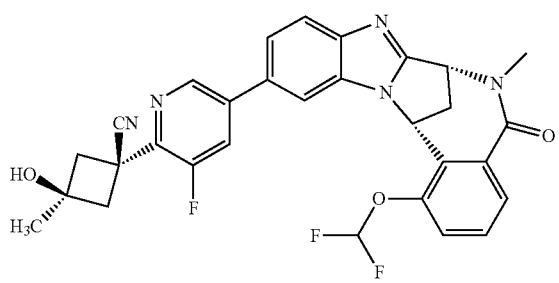 [SMILES: CN1C(=O)c2cccc(OC(F)F)c2[C@H]2C[C@@H]1c1nc3ccc(-c4cnc([C@]5(O)C[C@@](C)(C#N)C5)c(F)c4)cc3n12]

Intermediate 2 (95 mg, 0.16 mmol), Intermediate 11 (50 mg, 0.18 mmol), potassium phosphate tribasic (100 mg, 0.46 mmol) and tricyclohexylphosphonium tetrafluoroborate (10 mg, 0.026 mmol) were dissolved in 1,4-dioxane (2.0 mL) and water (0.5 mL) added. The reaction was degassed with three cycles of vacuum and nitrogen before the addition of tris(dibenzylideneacetone)dipalladium(0) (10 mg, 0.011 mmol). The reaction was again degassed/refilled with nitrogen and heated to 100° C. for 5 h before being allowed to cool to r.t. Reaction was diluted with DCM and water, passed through a phase separator and the organic phase reduced under vacuum. Purified with flash column chromatography on silica (gradient elution with 50-100% EtOAc/isohexane t and then 0-15% MeOH/DCM). Desired fractions eluting at approx. 10% MeOH/DCM were combined and concentrated under vacuum to give a pale yellow foam, further purified by preparative HPLC and freeze-dried overnight to afford the title compound as a white powder (20 mg, 23%)

LCMS (ES+) [M+H]$^+$ 560, RT 1.81 minutes (Method 1).

$^1$H NMR (400 MHz, DMSO-d$_6$) δ 8.75 (t, J=1.7 Hz, 1H), 8.31-8.25 (m, 1H), 8.12 (dd, J=11.8, 1.9 Hz, 1H), 7.90-7.68 (m, 3H), 7.65 (dd, J=8.6, 1.7 Hz, 1H), 7.53-7.49 (m, 2H), 6.31 (d, J=7.1 Hz, 1H), 5.55 (s, 1H), 5.27 (d, J=7.1 Hz, 1H), 3.65-3.44 (m, 1H), 3.37 (s, 3H), 3.04 (d, J=12.2 Hz, 2H), 2.85 (d, J=13.3 Hz, 3H), 1.10 (s, 3H)

The invention claimed is:

1. A compound of formula (I), or a pharmaceutically acceptable salt thereof:

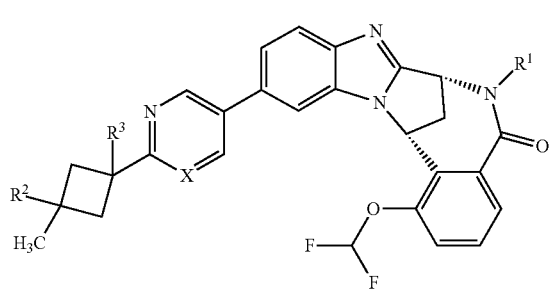

(I)

wherein
X represents N or C—F;
R$^1$ represents hydrogen or methyl or an isotopic variant thereof;
R$^2$ represents hydroxy or cyano;
R$^3$ represents hydroxy or cyano; and
R$^2$ is different from R$^3$.

2. The compound as claimed in claim 1 represented by formula (IIA), or a pharmaceutically acceptable salt thereof:

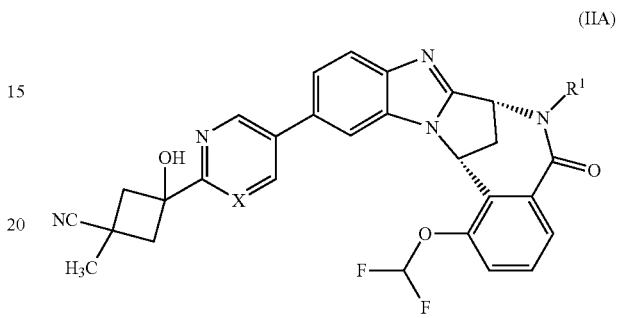

(IIA)

wherein X and R$^1$ are as defined in claim 1.

3. The compound as claimed in claim 1 represented by formula (IIB), or a pharmaceutically acceptable salt thereof:

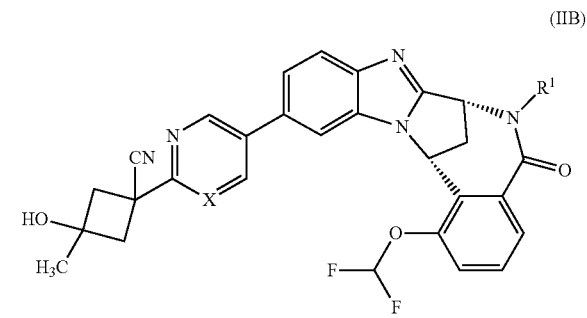

(IIB)

wherein X and R$^1$ are as defined in claim 1.

4. The compound as claimed in claim 1 represented by formula (I) or a pharmaceutically acceptable salt thereof, wherein R$^1$ represents hydrogen, —CH$_3$ or —CD$_3$.

5. The compound as claimed in claim 1 that is 3-[5-[(1R, 11R)-18-(difluoromethoxy)-13-oxo-12-(trideuteriomethyl)-2,9,12-triazapentacyclo[9.8.1.02,10.03,8.014, 19]icosa-3(8),4,6,9,14(19),15,17-heptaen-5-yl]pyrimidin-2-yl]-3-hydroxy-1-methylcyclobutane-1-carbonitrile;

3-[5-[(1R,11R)-18-(difluoromethoxy)-13-oxo-2,9,12-triazapentacyclo[9.8.1.02,10.03,8.014,19]icosa-3(8),4,6,9,14(19), 15,17-heptaen-5-yl]pyrimidin-2-yl]-3-hydroxy-1-methylcyclobutane-1-carbonitrile;

3-[5-[(1R,11R)-18-(difluoromethoxy)-6-fluoro-13-oxo-2,9,12-triazapentacyclo[9.8.1.02,10.03,8.014,19]icosa-3(8),4,6,9,14(19), 15,17-heptaen-5-yl]pyrimidin-2-yl]-3-hydroxy-1-methylcyclobutane-1-carbonitrile;

3-[5-[(1R,11R)-18-(difluoromethoxy)-12-methyl-13-oxo-2,9,12-triazapentacyclo[9.8.1.02,10.03,8.014, 19]icosa-3,5,7,9,14(19), 15,17-heptaen-5-yl]-3-fluoropyridin-2-yl]-3-hydroxy-1-methylcyclobutane-1-carbonitrile;

3-[5-[(1R,11R)-18-(difluoromethoxy)-13-oxo-2,9,12-triazapentacyclo[9.8.1.02,10.03,8.014,19]icosa-3,5,7,9, 14(19),15,17-heptaen-5-yl]-3-fluoropyridin-2-yl]-3-hydroxy-1-methylcyclobutane-1-carbonitrile;

1-[5-[(1R,11R)-18-(difluoromethoxy)-12-methyl-13-oxo-2,9,12-triazapentacyclo[9.8.1.02,10.03,8.014,19]icosa-3(8),4,6,9,14(19),15,17-heptaen-5-yl]pyrimidin-2-yl]-3-hydroxy-3-methylcyclobutane-1-carbonitrile; or 1-[5-[(1R,11R)-18-(difluoromethoxy)-12-methyl-13-oxo-2,9,12-triazapentacyclo[9.8.1.02,10.03,8.014,19]icosa-3(8),4,6,9,14(19),15,17-heptaen-5-yl]-3-fluoropyridin-2-yl]-3-hydroxy-3-methylcyclobutane-1-carbonitrile.

6. A pharmaceutical composition comprising a compound of formula (I) as defined in claim 1, or a pharmaceutically acceptable salt thereof, in association with a pharmaceutically acceptable carrier.

7. The pharmaceutical composition as claimed in claim 6 further comprising an additional pharmaceutically active ingredient.

8. A method for the treatment of Rheumatoid arthritis or Crohn's disease which comprises administering to a patient in need of such treatment an effective amount of the compound of formula (I) as defined in claim 1, or a pharmaceutically acceptable salt thereof.

* * * * *